US007914807B2

(12) United States Patent
Brito et al.

(10) Patent No.: US 7,914,807 B2
(45) Date of Patent: Mar. 29, 2011

(54) MEDICAL DEVICES HAVING IMPROVED PERFORMANCE

(75) Inventors: Shaina Brito, Winchester, MA (US); Frederick H. Strickler, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 929 days.

(21) Appl. No.: 11/714,029

(22) Filed: Mar. 5, 2007

(65) Prior Publication Data

US 2008/0220041 A1    Sep. 11, 2008

(51) Int. Cl.
*C08L 53/00* (2006.01)
*A61L 31/00* (2006.01)
*A61L 27/00* (2006.01)
*A61L 29/00* (2006.01)

(52) U.S. Cl. ............. 424/422; 424/423; 525/93; 525/96
(58) Field of Classification Search .................. 525/93, 525/96; 424/422, 423
See application file for complete search history.

(56) References Cited

U.S. PATENT DOCUMENTS

| | | | | |
|---|---|---|---|---|
| 4,319,014 | A | | 3/1982 | Peascoe et al. ............... 526/287 |
| 4,529,740 | A | * | 7/1985 | Trainor .......................... 521/81 |
| 4,617,337 | A | | 10/1986 | Lundberg et al. ............ 524/399 |
| 6,545,097 | B2 | | 4/2003 | Pinchuk et al. ............... 525/240 |
| 2004/0081829 | A1 | | 4/2004 | Klier et al. .................... 428/394 |
| 2004/0142910 | A1 | * | 7/2004 | Vachon et al. ................ 514/152 |
| 2005/0074495 | A1 | * | 4/2005 | Schwartz et al. ............. 424/484 |
| 2005/0119762 | A1 | * | 6/2005 | Zilla et al. .................. 623/23.75 |
| 2005/0239508 | A1 | | 10/2005 | Schwarz et al. |
| 2005/0288481 | A1 | | 12/2005 | DesNoyer et al. |
| 2007/0232169 | A1 | * | 10/2007 | Strickler et al. .............. 442/181 |
| 2007/0299155 | A1 | * | 12/2007 | Carpenter et al. ............ 523/105 |

FOREIGN PATENT DOCUMENTS

WO    2006014607 A2    2/2006
WO    2007124137 A2    11/2007

OTHER PUBLICATIONS

Shrirang V. Ranade et al., "Styrenic block copolymers for biomaterial and drug delivery applications," *Acta Biomater.*, Jan. 1, 2005(1), pp. 137-144.
Renu Virmani et al., "Localized Hypersensitivity and Late Coronary Thrombosis Secondary to a Sirolimus-Eluting Stent," *Circulation*, Feb. 17, 2004, 109(6), pp. 701-705.
Salamone, Joseph C., Ed., "Macromonomer TPE's," *Concise Polymeric Materials Encyclopedia*, CRC Press, Boca Raton, 1999, pp. 812-814.
Zhiqing Shi. et al., "Synthesis and Proton Conductivity of Partially Sulfonated Poly([vinylidene difluoride-*co*-hexafluoropropylene]-*b*-styrene) Block Copolymers," *Macromolecules*, 2005, 38(10), pp. 4193-4201.
Hee Jung Lee et. al., "Improved blood compatibility and decreased VSMC proliferation of surface-modified metal grafted with sulfonated PEG or heparin," *J. Biomater. Sci. Polymer Edn.*, 2002, vol. 13, No. 8, pp. 939-952.
Jeffrey Pyun et al, "Synthesis of Nanocomposite Organic/Inorganic Hybrid Materials Using Controlled/"Living" Radical Polymerization," *Chem. Mater.*, 2001, 13, pp. 3436-3448.
Ben Reeves, "Recent Advances in Living Free Radical Polymerization," Nov. 20, 2001. University of Florida.
T. Kowalewski et al., "Complex nanostructured materials from segmented copolymers prepared by ATRP," *Eur. Phys. J. E*, 2003, 10, pp. 5-16.
Yossef A. Elabd et al., "Sulfonation and characterization of poly(styrene-isobutylene-styrene) triblock copolymers at high ion-exchange capacities," *Polymer*, 45, 2004, pp. 3037-3043.
Chemical Resistance of Plastics and Elastomers (3rd Edition), By: Plastics Design Library Staff © 2001 William Andrew Publishing/ Plastics Design Library, Table of Contents, 3 pp.
Dan Hertz Jr., "Fluorine-containing elastomers introduction," *Technical report, Seals Eastern, Inc.*, 17 pages, Date unknown but at least as early as Nov. 2006. Available from http://www.sealseastern.com/ PDF/FluoroAcsChapter.pdf.

* cited by examiner

*Primary Examiner* — Jeffrey C Mullis
(74) *Attorney, Agent, or Firm* — Mayer & William PC; David B. Bonham; Keum J. Park (57) ABSTRACT

In accordance with various aspects of the invention, implantable and insertable medical devices are provided, which contain one or more polymeric regions. In one aspect, the polymeric regions comprise (a) a block copolymer that comprises a polyaromatic block and a polyalkene block admixed with (b) a sulfonated high Tg polymer. In another aspect, the polymeric regions comprise a block copolymer that comprises (a) a sulfonated polymer block and (b) fluorinated polymer block.

22 Claims, 1 Drawing Sheet

MEDICAL DEVICES HAVING IMPROVED PERFORMANCE

FIELD OF THE INVENTION

The present invention relates generally to medical devices, and more particularly to implantable or insertable medical devices.

BACKGROUND OF THE INVENTION

The implantation or insertion of medical devices into the body of a patient is common in the practice of modern medicine. For instance, in the past ten years stents have emerged as a prime therapy for arthroclerosis because they counteract the effects of intimal hyperplasia from balloon injury. Unfortunately, in-stent restenosis is a disease that may occur from the injury to the vessel wall. Drug eluting stents have a polymeric coating over the stent to release a drug at a prescribed rate for a given duration to counteract the effects of in-stent restenosis. The coating on the stent is in contact with the delivery system (e.g., balloon) along its inner diameter and in contact with the vessel wall along its outer diameter. It is advantageous to optimize the properties of the polymeric coating so as to control the release of drug, have optimum biocompatibility against the vessel wall, and be mechanically compatible with the surface of the balloon. Examples of drug eluting coronary stents include commercially available stents from Boston Scientific Corp. (TAXUS), Johnson & Johnson (CYPHER), and others. See S. V. Ranade et al., *Acta Biomater.* January 2005; 1(1): 137-44 and R. Virmani et al., *Circulation* Feb. 17, 2004, 109(6) 701-5.

Various types of polymeric materials have been used as drug-releasing reservoirs, including, for example, homopolymers such as poly(n-butyl methacrylate) and copolymers such as poly(ethylene-co-vinyl acetate) and poly(isobutylene-co-styrene), for example, poly(styrene-b-isobutylene-b-styrene) triblock copolymers (SIBS), which are described, for instance, in U.S. Pat. No. 6,545,097 to Pinchuk et al. SIBS triblock copolymers have a soft, elastomeric low glass transition temperature (Tg) midblock and hard elevated Tg endblocks. As with many block copolymers, SIBS tends to phase separate, with the elastomeric blocks aggregating to form elastomeric phase domains and the hard blocks aggregating to form hard phase domains. It has been hypothesized that, because each elastomeric block has a hard block at each end, and because different hard blocks within the same triblock copolymer are capable of occupying two different hard phase domains, the hard phase domains become physically crosslinked to one another via the elastomeric blocks. Moreover, because the crosslinks are not covalent in nature, they can be reversed, for example, by dissolving or melting the block copolymer. Consequently, SIBS copolymers are thermoplastic elastomers, in other words, elastomeric (i.e., reversibly deformable) polymers that form physical crosslinks which can be reversed by melting the polymer (or, in the case of SIBS, by dissolving the polymer in a suitable solvent).

SUMMARY OF THE INVENTION

In accordance with various aspects of the invention, implantable and insertable medical devices are provided, which contain one or more block-copolymer-containing polymeric regions.

In a first aspect, the polymeric regions comprise (a) a block copolymer that comprises a polyaromatic block and a polyalkene block admixed with (b) a sulfonated high Tg polymer.

In a second aspect, the polymeric regions comprise a block copolymer that comprises (a) a sulfonated polymer block and (b) fluorinated polymer block.

An advantage of the present invention is that a variety of physical and chemical characteristics may be tailored for a given polymeric region, including one or more of the following, among others: biocompatibility, surface tack, elasticity, water diffusivity, therapeutic agent diffusivity (where a therapeutic agent is present), and hydrophobic/hydrophilic balance (influencing, for example, wettability, as well as water diffusivity and therapeutic agent diffusivity, where a therapeutic agent is present).

These and other aspects, embodiments and advantages of the present invention will become immediately apparent to those of ordinary skill in the art upon review of the Detailed Description and Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

In accordance with various aspects of the invention, implantable and insertable medical devices are provided, which contain one or more block-copolymer-containing polymeric regions (e.g., an entire medical device, one or more portions of a medical device, etc.).

In a first aspect, the polymeric regions comprise (a) a block copolymer that comprises a polyaromatic block and a polyalkene block admixed with (a) a sulfonated high Tg polymer.

Figure 1:
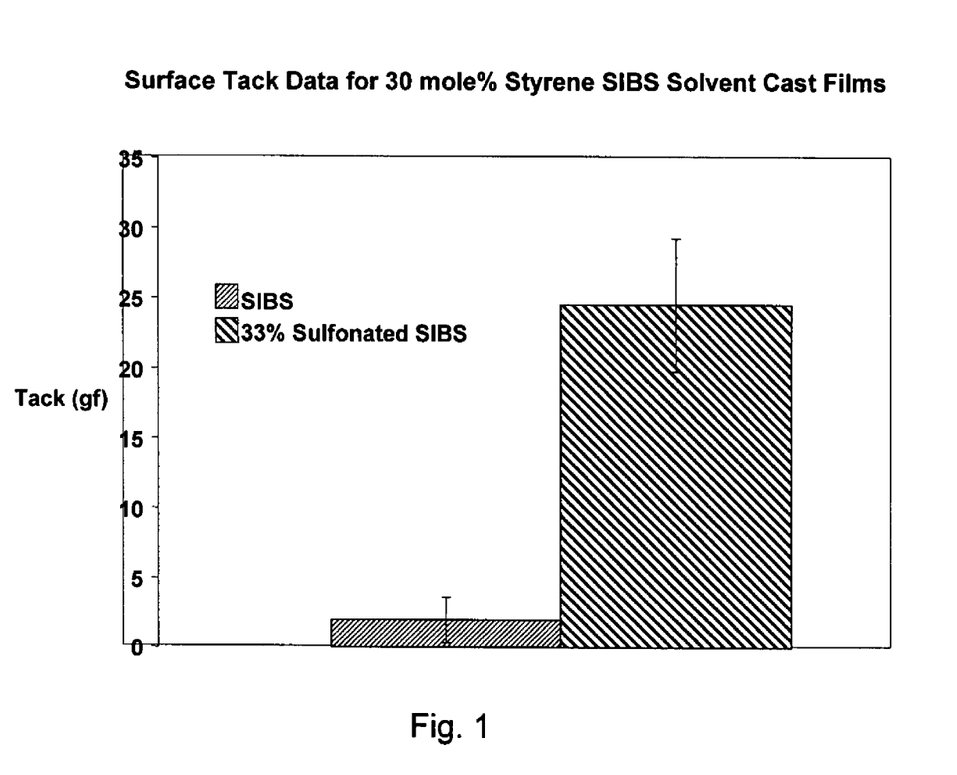
FIG. 1 is a bar graph depicting surface tack of 30 mol % SIBS in both sulfonated and non-sulfonated forms.

SIBS is one example of a block copolymer of this type, among many others. As noted above, SIBS copolymers are useful in drug-releasing coronary stent coatings. In addition to its ability to serve as a drug delivery reservoir, SIBS has excellent biocompatibility, elasticity, strength, and processability. Where a SIBS coating is deployed on a stent, the coating on the inner diameter of the stent is typically in contact with the delivery system (e.g., a balloon) and subsequently the bloodstream, whereas the coating on the outer diameter is deployed against the body lumen wall (e.g., a blood vessel wall). In this regard, surface coatings of sulfonated copolymers (e.g., sulfonated PEO) have been shown to have anti-thrombogenic effects in vivo as measured by a reduction of platelet and vascular smooth muscle cell adhesion. See, e.g., H. J. Lee et. al., *J. Biomater. Sci. Polymer Edn.*, Vol. 13, No. 8, pp. 939-952 (2002). While sulfonated SIBS has elastomeric and substrate adhesion properties desired for a conformal or abluminal stent coating, as seen from FIG. 1, this material has increased surface tack compared to non-sulfonated SIBS with comparable styrene levels (30 mol %). Surface tack is an important property for stent coatings, as high surface tack can cause defects in the coating after the stent is expanded/deployed. The non-sulfonated SIBS in FIG. 1 was formed by cationic polymerization along the lines described in U.S. Pat. No. 6,545,097 to Pinchuk et al. To create the sulfonated form, this polymer was sulfonated along the lines described in Z. Shi et al., *Macromolecules* 2005, 38, 4193-4201.

Thus, accordance with the above-described first aspect of the invention, the polymeric region is supplied with sulfonate groups, not by sulfonating the block copolymer, but rather by supplying sulfonate groups in conjunction with a distinct polymer, specifically, a sulfonated high Tg polymer.

In a second aspect of the invention, on the other hand, the polymeric region is supplied with sulfonate groups by including them within a block copolymer that comprises (a) a sulfonated polymer block and (b) fluorinated polymer block. As is well known, fluorinated polymer blocks typically have inherently surface energies (and thus low surface tack), relative to various other polymer blocks, including polyalkene polymer blocks such as polyisobutylene.

Examples of medical devices for the practice of the present invention include implantable or insertable medical devices, for example, stents (including coronary vascular stents, peripheral vascular stents, cerebral, urethral, ureteral, biliary, tracheal, gastrointestinal and esophageal stents), stent coverings, stent grafts, vascular grafts, valves including heart valves and vascular valves, abdominal aortic aneurysm (AAA) devices (e.g., AAA stents, AAA grafts, etc.), vascular access ports, dialysis ports, embolization devices including cerebral aneurysm filler coils (including Guglilmi detachable coils and metal coils), embolic agents, tissue bulking devices, catheters (e.g., renal or vascular catheters such as balloon catheters and various central venous catheters), guide wires, balloons, filters (e.g., vena cava filters and mesh filters for distil protection devices), septal defect closure devices, myocardial plugs, patches, pacemakers, lead coatings including coatings for pacemaker leads, defibrillation leads and coils, ventricular assist devices including left ventricular assist hearts and pumps, total artificial hearts, shunts, anastomosis clips and rings, cochlear implants, and tissue engineering scaffolds for cartilage, bone, skin and other in vivo tissue regeneration, urethral slings, hernia "meshes", artificial ligaments, orthopedic prosthesis, dental implants, biopsy devices, as well as any coated substrate (which can comprise, for example, metals, polymers, ceramics and combinations thereof) that is implanted or inserted into the body.

In some embodiments, the polymeric regions of the present invention correspond to an entire medical device. In other embodiments, the polymeric regions correspond to one or more portions of a medical device. For instance, the polymeric regions can be in the form of medical device components, in the form of one or more fibers which are incorporated into a medical device, in the form of one or more polymeric layers formed over all or only a portion of an underlying substrate, and so forth. Materials for use as underlying medical device substrates include ceramic, metallic and polymeric substrates. The substrate material can also be a carbon- or silicon-based material, among others. Layers can be provided over an underlying substrate at a variety of locations and in a variety of shapes (e.g., in the form of a series of rectangles, stripes, or any other continuous or non-continuous pattern). As used herein a "layer" of a given material is a region of that material whose thickness is small compared to both its length and width. As used herein a layer need not be planar, for example, taking on the contours of an underlying substrate. Layers can be discontinuous (e.g., patterned).

As used herein, a "polymeric region" is a region (e.g., an entire device, a device component, a device coating layer, etc.) that contains polymers, for example, from 50 wt % or less to 75 wt % to 90 wt % to 95 wt % to 97.5 wt % to 99 wt % or more polymers.

As used herein, "polymers" are molecules containing multiple copies (e.g., from 5 to 10 to 25 to 50 to 100 to 250 to 500 to 1000 or more copies) of one or more constitutional units, commonly referred to as monomers. As used herein, the term "monomers" may refer to the free monomers and to those that have been incorporated into polymers, with the distinction being clear from the context in which the term is used.

Polymers may take on a number of configurations, which may be selected, for example, from linear, cyclic and branched configurations, among others. Branched configurations include star-shaped configurations (e.g., configurations in which three or more chains emanate from a single branch point), comb configurations (e.g., configurations having a main chain and a plurality of side chains, also referred to as "graft" configurations), dendritic configurations (e.g., arborescent and hyperbranched polymers), and so forth.

As used herein, "homopolymers" are polymers that contain multiple copies of a single constitutional unit (i.e., monomer). "Copolymers" are polymers that contain multiple copies of at least two dissimilar constitutional units, examples of which include random, statistical, gradient, periodic (e.g., alternating) and block copolymers.

As used herein, "block copolymers" are copolymers that contain two or more polymer blocks that differ in composition, for instance, because a constitutional unit (i.e., monomer) is found in one polymer block that is not found in another polymer block. As used herein, a "polymer block" or "block" is a grouping of constitutional units (e.g., 5 to 10 to 25 to 50 to 100 to 250 to 500 to 1000 or more units). Blocks can be unbranched or branched. Blocks can contain a single type of constitutional unit (also referred to herein as "homopolymeric blocks") or multiple types of constitutional units (also referred to herein as "copolymeric blocks") which may be present, for example, in a random, statistical, gradient, or periodic (e.g., alternating) distribution.

As used herein, a "chain" is a linear polymer or a portion thereof, for example, a linear block.

Polymers and polymer blocks for use in the present invention include low glass transition temperature (Tg) polymers and polymer blocks and high Tg polymers and polymer blocks. As used herein, a "low Tg polymer" or a "low Tg polymer block" is one that displays a Tg that is below body temperature, more typically from 35° C. to 20° C. to 0° C. to −25° C. to −50° C. or below. Conversely, as used herein, a "high Tg polymer" or a "high Tg polymer block" is one that displays a Tg that is above body temperature, more typically from 40° C. to 50° C. to 75° C. to 100° C. or above. Tg can be measured by differential scanning calorimetry (DSC).

As noted above, in accordance with various aspects of the invention, medical devices are provided, which contain one or more polymeric regions. In one aspect, the polymeric regions comprise a block copolymer that comprises (a) a sulfonated polymer block and (b) a fluorinated polymer block.

Fluorinated monomers for use in forming the fluorinated polymer blocks may be selected from one or more suitable members of the following, among others (some of which are presented with a published Tg for the homopolymer): (a) partially and fully fluorinated alkene monomers (which consist of carbon, fluorine and optionally hydrogen), such as vinyl fluoride (Tg 40° C.), vinylidene fluoride (Tg −40° C.), trifluoroethylene, tetrafluoroethylene, and hexafluoropropylene, (b) partially and fully halogenated alkene monomers having fluorine and chlorine substitution (which consist of carbon, fluorine, chlorine and optionally hydrogen) such as chlorotrifluoroethylene, (c) fluorinated esters including acrylate esters with partially and fully fluorinated alkyl groups such as 2,2,2-trifluoroethyl acrylate (Tg −10° C.) and pentafluoroethyl acrylate, methacrylate esters with partially and fully fluorinated alkyl groups such as 2,2,2-trifluoroethyl methacrylate and pentafluoroethyl methacrylate, and vinyl esters with partially and fully fluorinated alkyl groups such as vinyl trifluoroacetate (Tg 46° C.), (d) vinyl ethers with partially and fully fluorinated alkyl groups such as perfluoromethyl vinyl ether, perfluoroethyl vinyl ether and perfluoropropyl vinyl ether.

Sulfonated polymer blocks include those that are formed by polymerizing sulfonated monomers and those that are sulfonated after the monomers have been incorporated by polymerization. Thus, sulfonated monomers include those that are sulfonated at the time of monomer incorporation (polymerization) and those that are formed after monomer incorporation.

Examples of the former include vinyl sulfonic acid, styrene sulfonic acid, allyl sulfonic acid, sulfoethyl methacrylate, sulfopropyl methacrylate, 2-acrylamido-2-methylpropane sulfonic acid (AMPS), 1-allyloxy-2-hydroxypropane sulfonic acid, and 3-allyloxy-2-hydroxypropane sulfonic acid, among others, as well as salts thereof, including ammonium, alkali metal (e.g., Li, Na, K, etc.) and alkaline earth metal (Be, Mg, Ca, etc.) salts, among others.

Examples of the latter include readily sulfonatable monomers such as aromatic monomers, for example, (1) vinyl aromatic monomers such as (a) unsubstituted vinyl aromatics, such as styrene (Tg 100° C.) and 2-vinyl naphthalene (Tg 151° C.), (b) vinyl substituted aromatics such as alpha-methyl styrene, (c) ring-substituted vinyl aromatics including ring-alkylated vinyl aromatics such as 3-methylstyrene (Tg 97° C.), 4-methylstyrene (Tg 97° C.), 2,4-dimethylstyrene (Tg 112° C.), 2,5-dimethylstyrene (Tg 143° C.), 3,5-dimethylstyrene (Tg 104° C.), 2,4,6-trimethylstyrene (Tg 162° C.), and 4-tert-butylstyrene (Tg 127° C.), ring-alkoxylated vinyl aromatics, such as 4-methoxystyrene (Tg 113° C.) and 4-ethoxystyrene (Tg 86° C.), ring-halogenated vinyl aromatics such as 2-chlorostyrene (Tg 119° C.), 3-chlorostyrene (Tg 90° C.), 4-chlorostyrene (Tg 110° C.), 2,6-dichlorostyrene (Tg 167° C.) and 4-bromostyrene (Tg 118° C.), ring-ester-substituted vinyl aromatics such as 4-acetoxystyrene (Tg 116° C.), ring-hydroxylated vinyl aromatics such as 4-hydroxystyrene (Tg 174° C.), ring-amino-substituted vinyl aromatics including 4-amino styrene, ring-silyl-substituted styrenes such as p-dimethylethoxy siloxy styrene, (d) unsubstituted and substituted vinyl pyridines such as 2-vinyl pyridine (Tg 104° C.) and 4-vinyl pyridine (Tg 142° C.), (e) vinyl aromatic esters such as vinyl benzoate (Tg 71° C.) and vinyl 4-tert-butyl benzoate (Tg 101° C.), and (f) other vinyl aromatic monomers such as vinyl carbazole (Tg 227° C.) and vinyl ferrocene (Tg 189° C.), (2) aromatic acrylates such as benzyl acrylate (Tg 6° C.), (3) aromatic methacrylates such as phenyl methacrylate (Tg 110° C.) and benzyl methacrylate (Tg 54° C.). For ring substituted aromatics, the rate and degree of the sulfonation will depend on the nature of the substituents. For example, aromatics with electron donating groups (e.g., amines, hydroxyls, alkyl, alkoxy, etc.) will typically react faster than unsubstituted aromatics, whereas aromatics with electron withdrawing groups (e.g., halogen, nitro, nitrile, etc.) will typically decrease the rate of sulfonation.

Examples of the latter further include diene monomers such as 1,3-butadiene, 2-methyl-1,3-butadiene (isoprene), 2,3-dimethyl-1,3-butadiene, 2-ethyl-1,3-butadiene, 1,3-pentadiene, 2-methyl-1,3-pentadiene, 4-butyl-1,3-pentadiene, 2,3-dibutyl-1,3-pentadiene, 2-ethyl-1,3-pentadiene, 1,3-hexadiene, 1,3-octadiene, 3-butyl-1,3-octadiene, cis-chlorobutadiene (Tg −20° C.), and trans-chlorobutadiene (Tg −40° C.), among others.

The fluorinated polymer block, the sulfonated polymer block (or its non-sulfonated counterpart) may independently be, for example, low or high Tg polymer blocks.

For instance, in certain embodiments, the block copolymer may comprise one or more high Tg fluorinated polymer blocks and one or more low Tg sulfonated polymer blocks.

In certain other embodiments, the block copolymer may comprises one or more low Tg fluorinated polymer blocks and one or more high Tg sulfonated polymer blocks.

For example, in some embodiments, the block copolymer may contain (a) one or more sulfonated polystyrene blocks and (b) one or more low Tg fluorinated polymer blocks selected from a polyvinylidene fluoride block, a polyhexafluoropropylene block, a poly(vinylidene fluoride-co-hexafluoropropylene) block, a poly(tetrafluoroethylene-co-perfluoromethyl vinyl ether) block, a poly(vinylidene fluoride-co-chlorotrifluoroethylene) block, a poly(tetrafluoroethylene-co-propylene) block, and a poly(vinylidene fluoride-co-hexafluoropropylene-co-tetrafluoroethylene) block, a poly(vinylidene fluoride-co-fluorinated vinyl ether-co-tetrafluoroethylene) block, a poly(vinylidene fluoride-co-propylene-co-tetrafluoroethylene) block, and a poly(vinylidene fluoride-co-fluorinated vinyl ether-co-hexafluoropropylene-co-ethylene-co-tetrafluoroethylene) block.

In certain embodiments of the invention, the block copolymer comprises at least one low Tg block and at least two high Tg blocks, with at least a portion of a low Tg block separating two high Tg blocks (in other words the high Tg blocks are interconnected via a low Tg block). Examples of this architecture include, for example, the following configurations, among many others, in which low Tg polymer blocks are designated "L" and high Tg polymer blocks are designated "H": (a) block copolymers having alternating chains of the type HLH, $(HL)_m$, $L(HL)_m$ and $H(LH)_m$ where m is a positive whole number of 2 or more, (b) multiarm (including star) copolymers such as $X(LH)_m$, where m is a positive whole number of 2 or more and where X is a hub species (e.g., an initiator molecule residue, a linking residue, etc.), which is typically ignored in block copolymer terminology, for example, with $X(LH)_2$ described as a triblock copolymer of the formula HLH and (c) comb copolymers having an L chain backbone and multiple H side chains. Polymers of this type are capable of demonstrating high strength and elastomeric properties, while at the same time being processable using techniques such as solvent- and/or melt-based processing techniques.

In another aspect, polymeric regions for medical devices are provided, which comprise (a) a block copolymer that comprises a polyalkene block and a polyaromatic block admixed with (b) a sulfonated high Tg polymer.

Examples of polyalkene blocks may be selected for example, for one or more of the following, among others: mono-unsaturated C2-C10 alkenes such as ethylene, propylene (Tg −8 to −13° C.), isobutylene (Tg −73° C.), 1-butene (Tg −24° C.), 4-methyl pentene (Tg 29° C.), 1-octene (Tg −63° C.) and other α-olefins, and C4-C15 dienes such as 1,3-butadiene, 2-methyl-1,3-butadiene (isoprene), 2,3-dimethyl-1,3-butadiene, 2-ethyl-1,3-butadiene, 1,3-pentadiene, 2-methyl-1,3-pentadiene, 4-butyl-1,3-pentadiene, 2,3-dibutyl-1,3-pentadiene, 2-ethyl-1,3-pentadiene, 1,3-hexadiene, 1,3-octadiene, and 3-butyl-1,3-octadiene.

Examples of polyaromatic blocks include those formed from one or more of the following monomers, among others: (1) vinyl aromatic monomers included (a) unsubstituted vinyl aromatics, such as styrene (Tg 100° C.) and 2-vinyl naphthalene (Tg 151° C.), (b) vinyl substituted aromatics such as alpha-methyl styrene, (c) ring-substituted vinyl aromatics including ring-alkylated vinyl aromatics such as 3-methylstyrene (Tg 97° C.), 4-methylstyrene (Tg 97° C.), 2,4-dimethylstyrene (Tg 112° C.), 2,5-dimethylstyrene (Tg 143° C.), 3,5-dimethylstyrene (Tg 104° C.), 2,4,6-trimethylstyrene (Tg 162° C.), and 4-tert-butylstyrene (Tg 127° C.), ring-alkoxylated vinyl aromatics, such as 4-methoxystyrene (Tg 113° C.) and 4-ethoxystyrene (Tg 86° C.), ring-halogenated vinyl aromatics such as 2-chlorostyrene (Tg 119° C.), 3-chlorostyrene (Tg 90° C.), 4-chlorostyrene (Tg 110° C.), 2,6-dichlorostyrene (Tg 167° C.), 4-bromostyrene (Tg 118° C.) and 4-fluorostyrene (Tg 95° C.), ring-ester-substituted vinyl aromatics such as 4-acetoxystyrene (Tg 116° C.), ring-hydroxylated vinyl aromatics such as 4-hydroxystyrene (Tg 174° C.), ring-amino-substituted vinyl aromatics including 4-amino styrene, ring-silyl-substituted styrenes such as p-dimethylethoxy siloxy styrene, (d) unsubstituted and substituted vinyl pyridines such as 2-vinyl pyridine (Tg 104° C.) and 4-vinyl pyridine (Tg 142° C.), (e) vinyl aromatic esters such as vinyl benzoate (Tg 71° C.) and vinyl 4-tert-butyl benzoate (Tg 101° C.), and (f) other vinyl aromatic monomers such as vinyl carbazole (Tg 227° C.) and vinyl ferrocene (Tg 189° C.), (2) aromatic acrylates such as benzyl acrylate (Tg 6° C.) and (3) aromatic methacrylates such as phenyl methacrylate (Tg 110° C.) and benzyl methacrylate (Tg 54° C.).

Examples of sulfonated high Tg polymers include high Tg sulfonated homopolymers and copolymers.

In some embodiments, a sulfonated high Tg homopolymer may be formed by polymerizing a sulfonated monomer (e.g., a sulfonated aromatic monomer such as styrene sulfonic acid or a salt thereof). In other embodiments a sulfonated high Tg homopolymer may be formed by sulfonating a suitable homopolymer, for example, an aromatic homopolymer formed from a suitable aromatic monomer (e.g., selected from sulfonatable members of the forgoing aromatic monomers).

In some embodiments, a sulfonated high Tg copolymer may be formed by copolymerizing (a) a sulfonated monomer (e.g., a sulfonated aromatic monomer) and (b) one or more comonomers selected from sulfonated comonomers, non-sulfonated comonomers (e.g., high Tg non-sulfonated comonomers selected from suitable members of those set forth below), or both. In other embodiments a sulfonated high Tg copolymer may be formed by sulfonating a suitable copolymer, for example, a copolymer that comprises (a) a sulfonatable monomer and (b) one or more comonomers selected from sulfonatable comonomers, non-sulfonatable comonomers (e.g., selected from non-sulfonatable members of the high Tg comonomers set forth below), or both.

Clearly, the monomers selected for the above methods should be compatible with the polymerization and/or sulfonation conditions that are employed.

Examples of non-sulfonated and non-sulfonatable comonomers may be selected from suitable members of the following, among others: (1) unsaturated anhydride monomers such as maleic anhydride, (2) high Tg vinyl monomers including (a) high Tg vinyl aromatics such as those set forth above, (b) high Tg vinyl esters such as vinyl cyclohexanoate (Tg 76° C.), vinyl pivalate (Tg 86° C.), vinyl trifluoroacetate (Tg 46° C.), vinyl butyral (Tg 49° C.), (c) high Tg vinyl amines, (d) high Tg vinyl halides such as vinyl chloride (Tg 81° C.) and vinyl fluoride (Tg 40° C.), (e) high Tg alkyl vinyl ethers such as tert-butyl vinyl ether (Tg 88° C.) and cyclohexyl vinyl ether (Tg 81° C.), (f) other vinyl monomers such as vinyl pyrrolidone; (3) high Tg methacrylic monomers including (a) methacrylic acid anhydride (Tg 159° C.), (b) methacrylic acid esters (methacrylates) including (i) alkyl methacrylates such as methyl methacrylate (Tg 105-120° C.), ethyl methacrylate (Tg 65° C.), isopropyl methacrylate (Tg 81° C.), isobutyl methacrylate (Tg 53° C.), t-butyl methacrylate (Tg 118° C.) and cyclohexyl methacrylate (Tg 92° C.), (ii) hydroxyalkyl methacrylates such as 2-hydroxyethyl methacrylate (Tg 57° C.) and 2-hydroxypropyl methacrylate (Tg 76° C.), (iii) additional methacrylates including isobornyl methacrylate (Tg 110° C.) and trimethylsilyl methacrylate (Tg 68° C.), and (c) other methacrylic-acid derivatives including methacrylonitrile (Tg 120° C.); (4) high Tg acrylic monomers including (a) acrylic acid esters such as tert-butyl acrylate (Tg 43-107° C.), hexyl acrylate (Tg 57° C.) and isobornyl acrylate (Tg 94° C.) and (b) other acrylic-acid derivatives including acrylonitrile (Tg 125° C.).

In a specific embodiment, polymeric regions for medical devices are provided, which comprise (a) a block copolymer that comprises a polyalkene block and a polyaromatic block, for example, SIBS, among many others, blended with (b) a high Tg sulfonated polymer, for example, sulfonated polystyrene and/or sulfonated poly(styrene-co-maleic anhydride), among many others.

As will be appreciated by those of ordinary skill in the art, polymers employed in accordance with the present invention may be synthesized according to known methods, including cationic, anionic, and radical polymerization methods, particularly controlled/"living" cationic, anionic and radical polymerizations.

Living free radical polymerizations (also called controlled free radical polymerizations) may be employed in various embodiments of the invention, due to the undemanding nature of radical polymerizations in combination with the power to control polydispersities, architectures, and molecular eights that living processes provide. Monomers capable of free radical polymerization vary widely and may be selected from the following, among many others: vinyl aromatic monomers such as substituted and unsubstituted styrenes, substituted and unsubstituted alkenes such as ethylene, propylene, vinyl fluoride, vinylidene fluoride tetrafluoroethylene, triflourochloroethylene, vinyl chloride, vinylidene chloride, diene monomers such as 1,3-butadiene, isoprene, chloroprene and p-divinylbenzene, acrylic monomers, for example, acrylic acid, acrylamide, acrylonitrile, and acrylate esters such as butyl acrylate, methacrylic monomers, for example, methacrylic acid, methacrylonitrile, and methacrylate esters such as methyl methacrylate, beta-hydroxyethyl methacrylate, beta-dimethylaminoethyl methacrylate and ethylene glycol dimethacrylate, vinyl esters such as vinyl acetate, as well as other unsaturated monomers including iraconic acid, fumaric acid, maleic acid, N-vinylpyrrolidinone, N-vinylimidazole, and N,N'-methylenebis-acrylamide, among many others.

Specific examples of free radical polymerization processes include metal-catalyzed atom transfer radical polymerization (ATRP), stable free-radical polymerization (SFRP), including nitroxide-mediated processes (NMP), and degenerative transfer including reversible addition-fragmentation chain transfer (RAFT) processes. These methods are well-detailed in the literature and are described, for example, in an article by Pyun and Matyjaszewski, "Synthesis of Nanocomposite Organic/Inorganic Hybrid Materials Using Controlled/"Living" Radical Polymerization," *Chem. Mater.*, 13:3436-3448 (2001), B. Reeves, "Recent Advances in Living Free Radical Polymerization," Nov. 20, 2001. University of Florida, T. Kowalewski et al., "Complex nanostructured materials from segmented copolymers prepared by ATRP," *Eur. Phys. J E*, 10, 5-16 (2003).

ATRP is an appealing free radical polymerization technique, as it is tolerant of a variety of functional groups (e.g., alcohol, amine, and sulfonate groups, among others) and thus allows for the polymerization of many monomers. In monomer polymerization via ATRP, radicals are commonly generated using organic halide initiators and transition-metal complexes. Some typical examples of organic halide initiators include alkyl halides, haloesters (e.g., methyl 2-bromopropionate, ethyl 2-bromoisobutyrate, etc.) and benzyl halides (e.g., 1-phenylethyl bromide, benzyl bromide, etc.). A wide range of transition-metal complexes may be employed, including a variety of Ru—, Cu—, Os— and Fe-based systems. Examples of monomers that may be used in ATRP polymerization reactions include various unsaturated monomers such as alkyl methacrylates, alkyl acrylates, hydroxyalkyl methacrylates, vinyl esters, vinyl aromatic monomers, acrylamide, methacrylamide, acrylonitrile, and 4-vinylpyridine, among others. In ATRP, at the end of the polymerization, the polymer chains are capped with a halogen atom that can be readily transformed via $S_N1$, $S_N2$ or radical chemistry to provide other functional groups such as amino groups, among many others. Functionality can also be introduced into the polymer by other methods, for example, by employing initiators that contain functional groups which do not participate in the radical polymerization process. Examples include initiators with epoxide, azido, amino, hydroxyl, cyano, and allyl groups, among others. In addition, functional groups may be present on the monomers themselves.

Radical polymerizations based upon degenerative transfer systems generally employ transfer agents that contain moieties for both initiation and transfer, which are generated in the presence of radicals. Controlled radical polymerizations from degenerative transfer reactions have been performed with alkyl iodides, unsaturated methacrylate esters and thioesters as the transfer agents, among others. The use of thioesters in the radical polymerization of vinyl monomers results in a RAFT polymerization. The RAFT process has proven to be a versatile method, capable of polymerizing an extremely broad range of radical polymerizable monomers, including functional styrenes, acrylates, methacrylates, and vinyl esters, as well as water soluble monomers including ionic species such as sodium 2-acrylamido-2-methylpropanesulfonate (AMPS) and sodium 3-acrylamido-3-methylbutanoate (AMBA), among many others. Thio endgroups remaining after RAFT may be removed or displaced by other groups via radical chemistry.

SFRP polymerizations, including NMP, utilize alkoxyamine initiators and nitroxide persistent radicals to polymerize monomers such as styrenes and acrylates. A widely used nitroxide in the polymerization of styrene is 2,2,6,6-tetramethylpiperidinyloxy (TEMPO), although more recently developed nitroxides can also polymerize acrylates, acrylamides, 1,3-dienes and acrylonitrile based monomers, among others, in a controlled fashion. The resulting polymers contain terminal alkoxyamine groups, which may be transformed with radical chemistry. For example, maleic anhydride or maleimide derivatives may be added to the alkoxyamine, allowing the ready introduction of other functional groups.

Using the above and other polymerization techniques, various strategies may be employed for forming polymers in accordance with the invention.

Block copolymer may be prepared using various methods known in the polymerization art. Examples include successive monomer addition (a) from a mono- or di-functional intiator (e.g., for linear AB or ABA type block copolymers, respectively) and (b) tri-, quatra-, penta-, etc. functional initiators (e.g., for the formation of star copolymers).

Multiple types of polymerization techniques may be employed to form block copolymers. For example, radical polymerization techniques may be employed for block copolymers that contain monomers which are not radically polymerizable. In this regard, macroinitiators may be prepared using non-free-radical techniques, such as living anionic or cationic techniques by appropriate modification of the end groups of the resulting polymers, for instance, by the introducing at least one radically transferable atom, such as those found in alkyl halide groups such as benzylic halide and a-halo ester groups, among others. As another example, functional initiators (which may be protected) may be employed for a first type of polymerization process, followed by deprotection/conversion of the functional group(s), as needed, followed by polymerization via a second polymerization process. As another example, two or more previously formed polymers may be covalently attached to one another to create a block copolymer.

Comb-shaped block copolymers may be prepared, for example, by copolymerization of a macromonomer that has a terminal polymerizable group (e.g., a vinyl group, etc.) with another monomer (e.g., another vinyl monomer, etc.). Mixed side chains may be created using two differing macromonomers. The density of the side chains may be varied by varying the ratio of macromonomer to monomer. Comb-shaped copolymers may also be formed by growing polymer side chains from a polymer that has pendant functional groups along its length which act as polymerization initiators (e.g., alkyl halide groups for ATRP polymerization). Comb-shaped copolymers may further be formed by coupling end functional polymer chains with a polymer that has reactive functional groups along its length.

As noted above, sulfonated polymers for use in the present invention may be formed, for example, through the polymerization of sulfonated monomers and/or by sulfonating a suitable pre-existing polymer. Various methods are known for sulfonating polymers, including those with aromatic rings. Several such methods are described in Pub. No. US 2004/0081829 to Klier et al. For example, polymers may be sulfonated by contact with oleum (sulfur trioxide dissolved in sulfuric acid), by contact with a sulfonating complex comprising the reaction product of sulfur trioxide, chlorosulfonic acid or fuming sulfuric acid and a lower trialkyl phosphate or phosphate, or by a method in which sulfuric acid is combined with acetic anhydride followed by the addition of this mixture to a solution of the polymer in a chlorinated solvent. Salts of the resulting polymer may be prepared by reacting the polymer with a neutralizing agent or base (e.g., ammonia, alkylamine, ammonium hydroxide, sodium hydroxide, potassium hydroxide, etc.). For further information on these techniques see Pub. No. US 2004/0081829 and the references cited therein.

A specific procedure in which the styrenic monomers of SIBS are sulfonated to varying degrees (i.e., 13 to 82 mol % of the styrene) is set forth in Y. A. Elabd et al., *Polymer* 45 (2004) 3037-3043. Briefly, a solution of SIBS in methylene chloride was stirred and refluxed while a specified amount of acetyl sulfate in methylene chloride was slowly added to begin the sulfonation reaction. The acetyl sulfate in methylene chloride was prepared by adding acetic anhydride and sulfuric acid to chilled methylene chloride while stirring. Acetic anhydride reacts with sulfuric acid to form acetyl sulfate (which acts as the sulfonating agent) and acetic acid (a by product) and it removes excess water, thereby creating anhydrous conditions for sulfonation. The sulfonation reaction produces sulfonic acid groups which are generally substituted at the para position of the aromatic ring in the styrene block of the polymer.

In addition to one or more polymers, the polymeric regions for use in the medical devices of the present invention may optionally contain one or more therapeutic agents. "Therapeutic agents," "drugs," "pharmaceutically active agents," "pharmaceutically active materials," and other related terms may be used interchangeably herein.

The rate of release of therapeutic agent(s) from polymeric regions in accordance with the invention with depend, for example, on nature of the therapeutic agents(s), the nature of the polymer(s) (e.g., molecular weight, architecture, and monomer composition) within the polymeric regions, and the nature any other optional supplemental species. For instance, the nature of the therapeutic agents(s) (e.g., hydrophilic/hydrophobic) and the nature of the polymers (e.g., hydrophilic/hydrophobic/swellable) will have a significant effect upon the release of the drug (affecting, for example, the wettability of the polymeric regions, the water diffusivity, the therapeutic agent diffusivity, and so forth). The hydrophilic/hydrophobic/swellable nature of the polymeric region may also be modified by optionally adding supplemental hydrophobic and/or hydrophilic polymers to the polymeric region.

The therapeutic agent release profile may be controlled by other factors such as the size, number and/or position of the polymeric regions within the device. For example, the release profile of polymeric regions in accordance with the present invention may be modified by varying the thickness and/or surface areas of the same. Moreover, multiple polymeric regions may be employed to modify the release profile. For example, polymeric regions, either having the same or different content (e.g., different polymeric and/or therapeutic agent content), may be stacked on top of one another, may be positioned laterally with respect to one another, and so forth. Moreover, polymeric barrier layers may be provided over the therapeutic-agent-containing polymeric regions as described herein, or the polymeric regions described herein may be disposed over therapeutic agent containing regions as barrier layers.

A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition).

Exemplary therapeutic agents for use in conjunction with the present invention include the following: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine) (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.).

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin (sirolimus) and its analogs (e.g., everolimus, tacrolimus, zotarolimus, etc.), cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Preferred therapeutic agents include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

A wide range of therapeutic agent loadings may be used in conjunction with the medical devices of the present invention. Typical loadings range, for example, from than 1 wt % or less to 2 wt % to 5 wt % to 10 wt % to 25 wt % or more of the polymeric region.

Numerous techniques are available for forming polymeric regions in accordance with the present invention.

For example, where a polymeric region is formed from one or more polymers having thermoplastic characteristics, a variety of standard thermoplastic processing techniques may be used to form the polymeric region. Using these techniques, a polymeric region can be formed, for instance, by (a) first providing a melt that contains polymer(s) and any other optional agents such as therapeutic agents, and (b) subsequently cooling the melt. Examples of thermoplastic processing techniques include compression molding, injection molding, blow molding, spraying, vacuum forming and calendaring, extrusion into sheets, fibers, rods, tubes and other cross-sectional profiles of various lengths, and combinations of these processes. Using these and other thermoplastic processing techniques, entire devices or portions thereof can be made.

Other processing techniques besides thermoplastic processing techniques may also be used to form the polymeric regions of the present invention, including solvent-based techniques. Using these techniques, polymeric regions can be formed, for instance, by (a) first providing a solution or dispersion that contains polymer(s) and any optional agents such as therapeutic agents and (b) subsequently removing the solvent. The solvent that is ultimately selected will contain one or more solvent species, which are generally selected based on their ability to dissolve at least one of the polymer(s) that form the polymeric region, in addition to other factors, including drying rate, surface tension, etc. In certain embodiments, the solvent is selected based on its ability to dissolve the optional agents, if any. Thus, optional agents such as therapeutic agents may be dissolved or dispersed in the coating solution. Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In some embodiments of the invention, a polymer containing solution (where solvent-based processing is employed) or a polymer containing melt (where thermoplastic processing is employed) is applied to a substrate to form a polymeric region. For example, the substrate can correspond to all or a portion of an implantable or insertable medical device to which a polymeric coating is applied, for example, by spraying, extrusion, and so forth. The substrate can also be, for example, a template, such as a mold, from which the polymeric region is removed after solidification. In other embodiments, for example, extrusion and co-extrusion techniques, one or more polymeric regions are formed without the aid of a substrate. In a specific example, an entire medical device is extruded. In another, a polymeric coating layer is co-extruded along with and underlying medical device body.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising a polymer blend that comprises (a) a block copolymer that comprises a polyaromatic block and a polyalkene block and (b) a sulfonated high Tg polymer displaying a glass transition temperature that is 40° C. or more, wherein said sulfonated high Tg polymer is a sulfonated high Tg copolymer comprising a non-sulfonated comonomer selected from unsaturated anhydride monomers, high Tg vinyl ester monomers, high Tg vinyl amine monomers, high Tg alkyl vinyl ether monomers, high Tg methacrylic monomers, and vinyl pyrrolidone.

2. The medical device of claim 1, wherein said polyalkene block is a polyisobutylene block.

3. The medical device of claim 1, wherein said polyaromatic block comprises a vinyl aromatic monomer.

4. The medical device of claim 1, wherein said polyaromatic block is a polystyrene block.

5. The medical device of claim 1, wherein said block copolymer is a triblock copolymer.

6. The medical device of claim 1, wherein said block copolymer is a triblock copolymer comprising a polyisobutylene mid-block and two polystyrene end-blocks.

7. The medical device of claim 1, wherein said sulfonated high Tg polymer comprises a vinyl aromatic monomer.

8. An implantable or insertable medical device comprising a polymer blend that comprises (a) a block copolymer that comprises a polyaromatic block and a polyalkene block and (b) a sulfonated high Tg polymer displaying a glass transition temperature that is 40° C. or more, wherein said sulfonated high Tg polymer is sulfonated poly(styrene-co-maleic anhydride).

9. The medical device of claim 1, comprising a plurality of polymeric regions.

10. The medical device of claim 1, wherein said polymeric region is in the form of a layer that at least partially covers an underlying substrate.

11. The medical device of claim 1, wherein said polymeric region further comprises a therapeutic agent.

12. The medical device of claim 11, wherein said first therapeutic agent is selected from antiproliferative agents, antithrombotic agents, endothelial cell growth promoters, antimicrobial agents, analgesic agents, and anti-inflammatory agents.

13. The medical device of claim 1, wherein said medical device is a vascular medical device selected from a stent, a vascular graft, a stent graft, a heart valve, a vascular valve, a cerebral aneurysm filler coil, a filter, a guide wire, a balloon, and a catheter.

14. The medical device of claim 1, wherein said non-sulfonated comonomer is selected from unsaturated anhydride monomers, alkyl methacrylate monomers and hydroxyalkyl methacrylate monomers.

15. The medical device of claim 14, wherein said sulfonated high Tg polymer comprises a sulfonated aromatic monomer.

16. The medical device claim 15, wherein said medical device is a vascular medical device selected from a stent, a vascular graft, a stent graft, a heart valve, a vascular valve, a filter, a guide wire, a balloon, and a catheter.

17. The medical device of claim 14, wherein said non-sulfonated comonomer is selected from maleic anhydride, methyl methacrylate and 2-hydroxyethyl methacrylate.

18. The medical device of claim 17, wherein said sulfonated high Tg polymer comprises a sulfonated aromatic monomer.

19. The medical device claim 18, wherein said medical device is a vascular medical device selected from a stent, a vascular graft, a stent graft, a heart valve, a vascular valve, a filter, a guide wire, a balloon, and a catheter.

20. The medical device claim 8, wherein said medical device is a vascular medical device.

21. The medical device claim 20, wherein said vascular medical device is selected from a stent, a vascular graft, a stent graft, a heart valve, a vascular valve, a filter, a guide wire, a balloon, and a catheter.

22. The medical device of claim 1, wherein said sulfonated high Tg polymer comprises a sulfonated aromatic monomer, wherein said non-sulfonated comonomer is an unsaturated anhydride monomer, and wherein said medical device is a vascular medical device selected from a stent, a vascular graft, a stent graft, a heart valve, a vascular valve, a filter, a guide wire, a balloon, and a catheter.

* * * * *

UNITED STATES PATENT AND TRADEMARK OFFICE
CERTIFICATE OF CORRECTION

PATENT NO.         : 7,914,807 B2                                    Page 1 of 1
APPLICATION NO.    : 11/714029
DATED              : March 29, 2011
INVENTOR(S)        : Shaina Brito It is certified that error appears in the above-identified patent and that said Letters Patent is hereby corrected as shown below:

Specification, col. 6, line 7-8, after "may" change "comprises" to --comprise--.

Specification, col. 8, line 6, after "including" change "isobomyl" to --isobornyl--.

Specification, col. 10, line 8-9, after "and" change "a" to --$\alpha$--.

Signed and Sealed this
Twenty-seventh Day of September, 2011

David J. Kappos
*Director of the United States Patent and Trademark Office*